(12) United States Patent
Schwebel

(10) Patent No.: US 6,270,473 B1
(45) Date of Patent: Aug. 7, 2001

(54) HYPODERMIC JET INJECTOR AND DISPOSABLE AMPULE

(75) Inventor: Paul R. M. Schwebel, Indianapolia, IN (US)

(73) Assignee: Jettek, Inc., Indianapolis, IN (US)

( * ) Notice: Subject to any disclaimer, the term of this patent is extended or adjusted under 35 U.S.C. 154(b) by 0 days.

(21) Appl. No.: 08/913,826

(22) PCT Filed: Mar. 15, 1996

(86) PCT No.: PCT/US96/03618

§ 371 Date: Jan. 12, 1999

§ 102(e) Date: Jan. 12, 1999

(87) PCT Pub. No.: WO96/28203

PCT Pub. Date: Sep. 19, 1996

Related U.S. Application Data

(63) Continuation-in-part of application No. 08/404,581, filed on Mar. 15, 1995, now Pat. No. 5,503,628.

(51) Int. Cl.[7] .................................................. A61M 5/30

(52) U.S. Cl. ............................................. 604/69; 604/146

(58) Field of Search ................................ 604/68, 72, 69, 604/232, 325, 140–143, 134–137, 186–187, 151–157, 207–211, 218, 228, 181, 146; 222/325–326

(56) References Cited

U.S. PATENT DOCUMENTS

| | | |
|---|---|---|
| 2,322,245 | 6/1943 | Lockhart . |
| 3,308,818 | 3/1967 | Rutkowski . |
| 3,330,276 | 7/1967 | Gordon . |
| 3,330,277 | 7/1967 | Gabriels . |
| 3,335,722 | 8/1967 | Lowry et al. . |
| 3,521,633 | 7/1970 | Yahner . |
| 3,802,430 | 4/1974 | Schwebel et al. . |

(List continued on next page.)

OTHER PUBLICATIONS

User's manual, Medi–Jector LV, Derata Corporation (undated).

\* cited by examiner

Primary Examiner—Anhtuan T. Nguyen
Assistant Examiner—Michael M Thompson
(74) Attorney, Agent, or Firm—Woodard, Emhardt, Naughton, Moriarty & McNett

(57) ABSTRACT

A hypodermic jet injector employing self-contained, patient fillable, thin-walled disposable ampules. Each ampule includes an elongate plastic body with an injection orifice at a first end, an internal propellant at a closed second end, and a double piston slidably and sealingly mounted within the body entirely between the orifice and the internal propellant, and also includes an auxiliary access opening in the ampule side wall. An ampule chamber with a corresponding access opening in its side wall is provided to receive and support the thin-walled ampule. The main body of the ampule is molded with draft angles, and the double piston construction includes a soft rubber plunger and a relatively hard plunger to the front and rear, respectively, of the auxiliary access opening in the ampule, with the two plungers interconnected by a connecting rod spanning the central section of the ampule. The ampule chamber is provided with a draft angle in the front section of its bore adjacent to the soft plunger in the ampule, and a straight bore in the rear section adjacent to the hard plunger in the ampule. The injector includes a high-resolution metered filling device located parallel to the ampule chamber and including a piston engagement member which is laterally movable into contact with the connecting rod, which consequently moves under control of the filling device. The metered filling device includes a digital dosage display including a drum bearing a plurality of dosage values in integer form arranged in a spiral pattern on its surface, and a dosage selection window positioned so as to expose a single dosage value at a time.

16 Claims, 15 Drawing Sheets

U.S. PATENT DOCUMENTS

| | | |
|---|---|---|
| 3,908,651 | 9/1975 | Fudge . |
| 4,089,334 | 5/1978 | Schwebel et al. . |
| 4,124,024 | 11/1978 | Schwebel et al. . |
| 4,338,980 | 7/1982 | Schwebel et al. . |
| 4,507,113 | 3/1985 | Dunlap . |
| 4,518,385 | 5/1985 | Lindmayer et al. . |
| 4,564,363 | 1/1986 | Bagnall et al. . |
| 4,596,556 | 6/1986 | Morrow et al. . |
| 4,623,332 | 11/1986 | Lindmayer et al. . |
| 4,652,261 | 3/1987 | Mech et al. . |
| 4,662,878 | 5/1987 | Lindmayer . |
| 4,722,728 | 2/1988 | Dixon . |
| 4,790,824 | 12/1988 | Morrow et al. . |
| 4,863,873 | 9/1989 | Matson . |
| 4,883,483 | 11/1989 | Lindmayer . |
| 4,940,460 | 7/1990 | Casey et al. . |
| 4,941,880 | 7/1990 | Burns . |
| 4,944,726 | 7/1990 | Hilal et al. . |
| 4,997,496 | 3/1991 | Wehrli . |
| 5,024,656 | 6/1991 | Gasaway et al. . |
| 5,062,830 | 11/1991 | Dunlap . |
| 5,062,834 * | 11/1991 | Gross et al. . |
| 5,064,413 | 11/1991 | McKinnon et al. . |
| 5,080,648 | 1/1992 | D'Antonio . |
| 5,114,406 | 5/1992 | Gabriel et al. . |
| 5,279,586 | 1/1994 | Balkwill . |
| 5,312,335 | 5/1994 | McKinnon et al. . |
| 5,312,577 | 5/1994 | Peterson et al. . |
| 5,316,146 | 5/1994 | Graff . |
| 5,318,522 | 6/1994 | D'Antonio . |
| 5,350,336 * | 9/1994 | Schlosser et al. . |
| 5,354,287 * | 10/1994 | Wacks ................................. 604/232 |
| 5,380,296 | 1/1995 | Smedley et al. . |
| 5,503,628 * | 4/1996 | Fetters et al. .......................... 604/72 |

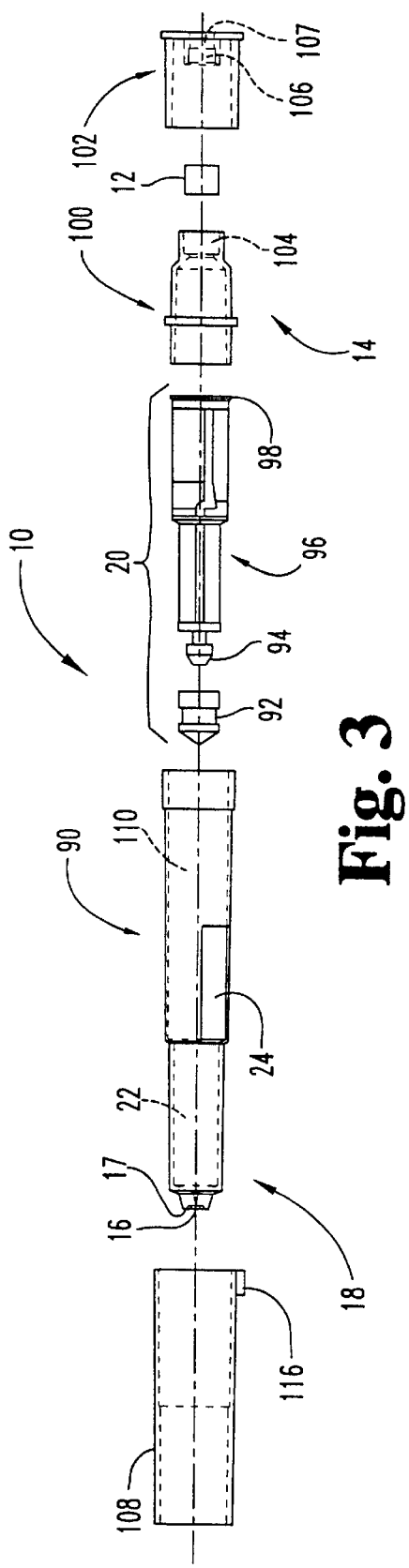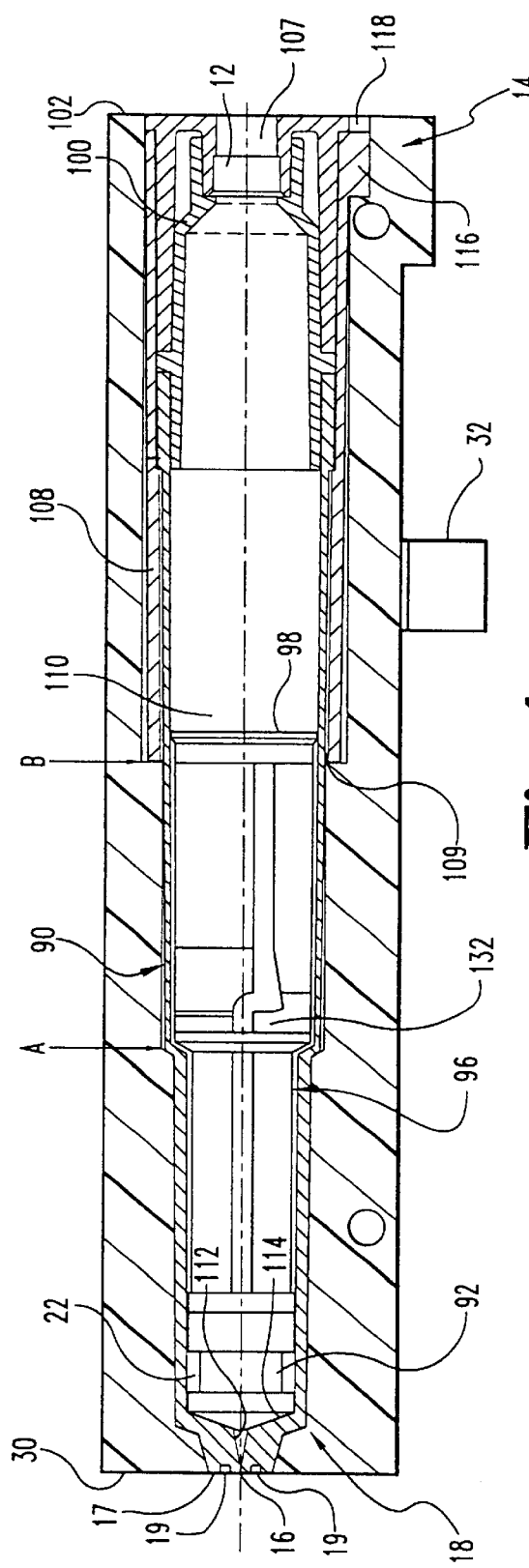

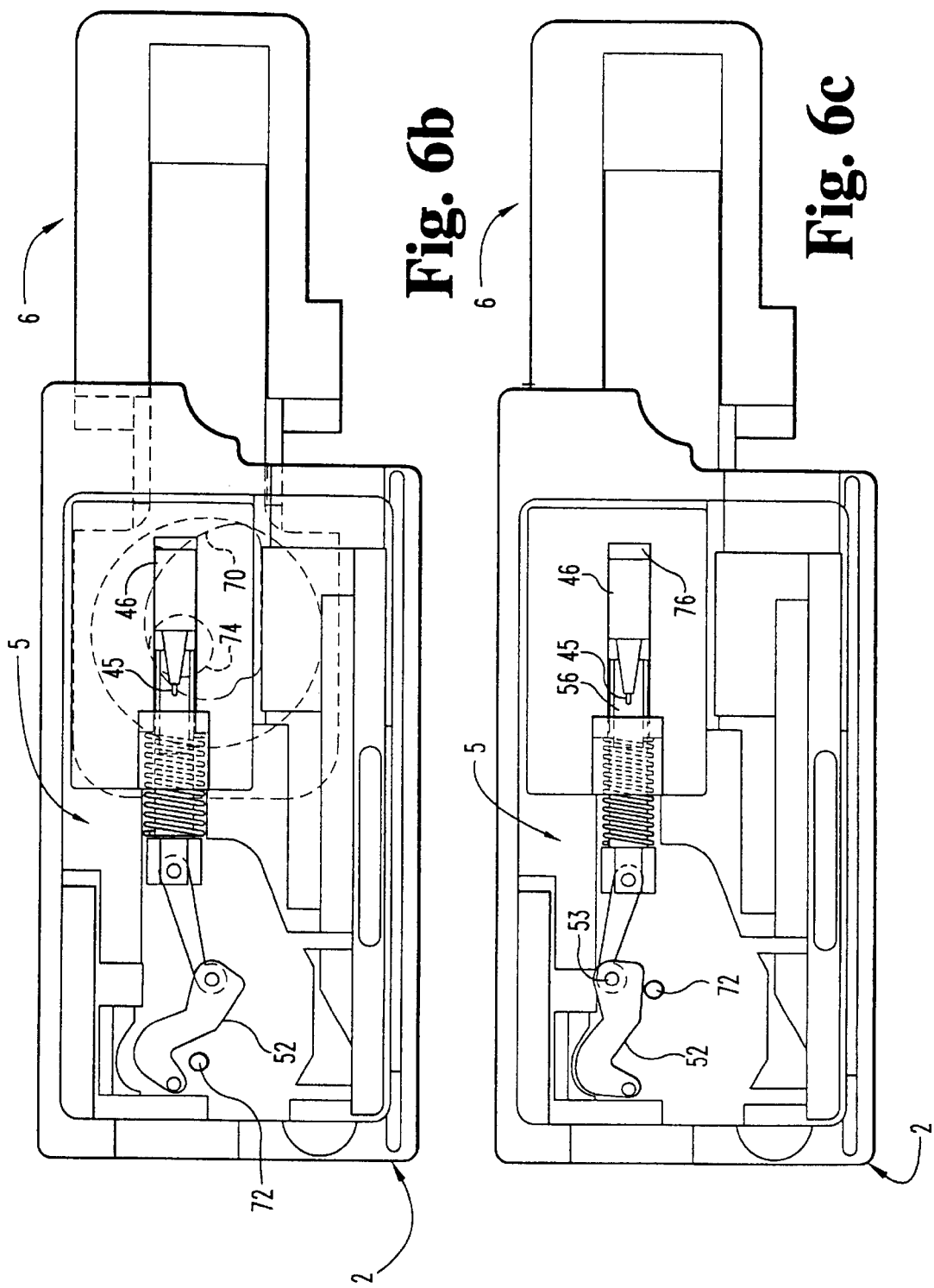

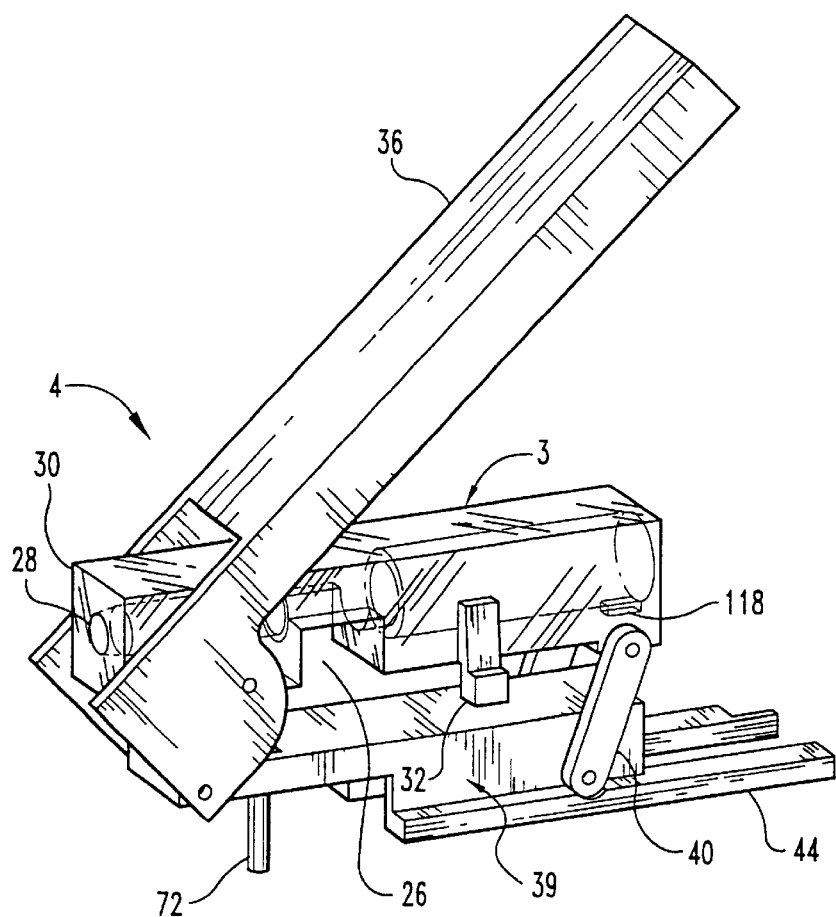
Fig.8
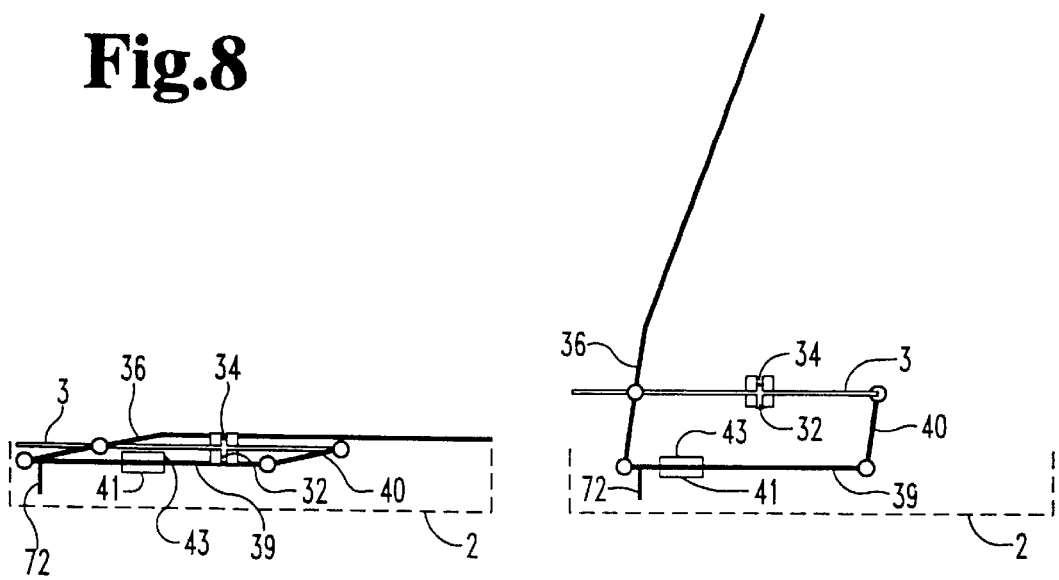
Fig. 9a     Fig. 9b

HYPODERMIC JET INJECTOR AND DISPOSABLE AMPULE

CROSS-REFERENCES TO RELATED APPLICATIONS

The application is a continuation-in-part of application Ser. No. 08/404,581 filed Mar. 15, 1995, now U.S. Pat. No. 5,503,628, issued Apr. 2, 1996.

BACKGROUND OF THE INVENTION

This invention relates generally to hypodermic injection devices, and more particularly to reusable hypodermic jet injectors, or needleless injectors, in which a dosage of medicine and a powering charge are contained within a disposable ampule.

Hypodermic injection devices capable of administering a dosage of medicine in the form of a fine, high-velocity jet delivered with sufficient force as to pass through skin tissue without the need of a hypodermic needle have been known since at least the 1960s. Perhaps the widest application of jet injectors is in the administration of insulin to individuals afflicted with diabetes, although such devices are also known for use in vaccinations as well as the administration of vitamins, anesthetics and other medicines in liquid form. Examples of jet injectors employing disposable ampules are disclosed in the following patents:

| U.S Pat. No. | Inventor | Issue Date |
| --- | --- | --- |
| 3,335,722 | Lowry et al. | Aug. 15, 1967 |
| 4,089,334 | Schwebel et al. | May 16, 1978 |
| 4,124,024 | Schwebel et al. | Nov. 7, 1978 |
| 4,518,385 | Lindmayer et al. | May 21, 1985 |
| 4,940,460 | Casey et al. | Jul. 10, 1990 |
| 5,312,335 | McKinnon et al. | May 17, 1994 |

Cost is normally a factor in the selection of any disposable device, and the cost of a disposable ampule is directly affected by the amount of material required for a particular ampule design as well as by manufacturing costs. In a number of the devices disclosed in the above patents a disposable ampule extends out of the forward end of the injector and, as such, must be designed to withstand the high internal pressures developed during injection. For example, disposable ampules have been made according to the principles of U.S. Pat. No. 4,089,334 to Schwebel et al. using polycarbonate, and a wall thickness of 0.100" has been found necessary with such a material. Reinforcement of the exposed exterior portion of an ampule as shown in U.S. Pat. No. 4,124,024 to Schwebel et al. can provide the strength required to withstand the pressures encountered during an injection, but at the cost of additional material incorporated into the ampule for reinforcement.

Lowry et al. discloses a disposable ampule having a stainless steel nose piece over the front end of a plastic sleeve, with the complete ampule except for the tip of the nose piece enclosed within the bore of the jet injector. Lowry et al. indicates a maximum thickness of about 0.020" for the stainless steel nose piece, and a greater thickness for the plastic sleeve. The ampule does not include a propellant charge; instead, a stopper of neoprene rubber or like elastomer is exposed at the rear of the ampule and is contacted from the rear by a piston which is forced forward into the ampule under pressure developed from the ignition of a propellant charge contained in a separate part of the hypodermic device.

Manufacturing concerns also come into play in connection with the cost of a disposable ampule. For example, the cycle time for a molding operation increases as a function of increased wall thickness and has a corresponding impact on labor costs and operating expenses.

In addition, we have discovered that injection molding of plastic ampules can be made more efficient by molding the ampules with draft angles, i.e., slightly tapered surfaces as opposed to uniform cylindrical surfaces. Draft angles on the inside and outside surfaces of an ampule will facilitate the separation of a newly molded ampule from an outer mold section or sections as well as from a core pin or insert or other inner mold part. It is further believed that such a construction will eliminate the need for a mold release, and thereby eliminate the associated material cost as well as the time required to apply the mold release to the mold surfaces and to thereafter remove all residual mold release from the molded ampule to prevent contamination.

Lindmayer et al discloses a syringe for a needleless injector in which the barrel of the syringe tapers slightly from front to rear and the injector barrel in which it fits is tapered internally to match the taper of the syringe barrel in order to use a thin-walled syringe barrel which is capable of resisting the high pressures required to create a high-velocity jet. The patent refers, without explanation or illustration, to a barrel and plunger tapered slightly for insertion into a similarly tapered casing of an injector, but the syringe plunger as disclosed is an elongated hard plastic body described as a cylindrical body with a conical front end for abutting the conical front end of the syringe barrel. Internally, the syringe barrel, which may be formed of polypropylene, similarly appears uniformly cylindrical in shape except for its conical front end. Without a draft angle on the inside wall surface of an ampule, however, injection molding of the ampule is made more difficult and consequently more expensive There is also an ever-increasing need for devices for rapidly and easily but very accurately preparing jet injectors for injection of a required medicine dosage, especially for home health care. Injectors suited for self-administration of medicine in a home care setting are desirable from a cost standpoint as well as from the standpoint of patient convenience, especially for long-term care which would otherwise necessitate frequent appointments with medical personnel. Cost constraints practically dictate reusable jet injectors, because it is impractical to dispose of a complete device after one use.

Some reusable injectors permit filling of medicine directly into an injection chamber, while others are designed to receive a prefilled ampule. After an injection with the former type, the injection chamber and any passageways leading to it from a supply vial inevitably contain some residual amount of medicine which can be difficult to remove. Periodic cleaning is typically required with such injectors, as exemplified by the Medi-Jector®, commercially available from Derata Corporation. Without proper cleaning, the residual amounts of medicine can lead to complications, particularly when different types of medicine are to be injected, as is fairly common in insulin administration regimens.

Patients are more likely to accept, and properly use, a jet injector that is simple to set up for use and that requires little or no cleaning after use. Prefilled ampules, including factory-filled ampules and ampules prefilled for a patient by a pharmacist, can help meet these criteria. Ampules capable of being filled by a pharmacist have an advantage over factory-filled ampules in that they do not require the pharmacist to maintain an inventory of ampules prefilled with various different amounts of different types of medicine. Physicians commonly prescribe different dosages of medicine for different medical conditions including the type and severity of an illness as well as the age and weight of an individual patient. In such situations it would be desirable to a pharmacist to have a single type of ampule that can accommodate different dosages. It would also be advantageous for patients in home care settings to be able to quickly and confidently fill such an ampule with a prescribed dosage from a conventional medicine vial, without help from medically trained personnel. However, this would require a filling mechanism that is fast and simple to use and still capable of precise measurement by untrained individuals.

Casey et al. discloses a patient-fillable ampule for a hypodermic injection device which can accommodate different dosages and which is filled via an adapter from a separate medicine bottle. The injection device assembly comprises a sleeve attached to a housing containing a gas cartridge and trigger mechanism, with the ampule contained within the sleeve during use. The sleeve must be separated from the housing to provide access to the ampule for replacement and/or filling. U.S. Pat. No. 4,338,980 to Schwebel et al. discloses a filling device for disposable ampules for use in jet injectors, but that device requires a special medicine vial as well as an ampule holder, a housing and a dispensing handle which a user must assemble in order to fill the ampule. Those afflicted with poor vision or poor memory, such as elderly diabetics, are likely to have difficulties with such a device, because the device with its multiple parts is separate from the jet injector and, thus, various parts of the device or the entire device may be misplaced between uses of the injector. Especially for such patients using patient-fillable ampules, it would be useful to have a hypodermic injector combined with a precise, easily used ampule-filling device in a single unit.

Ease of use for any patient-fillable ampule or jet injector is affected by the ease with which the user can read dosage indications during the filling process. Vernier scales, for example, are difficult for many people to read and understand, and other types of dosage indicators are hard to read for any patient with impaired vision. Such factors can reduce patient confidence in self-administration and, worse, can cause dosage errors.

SUMMARY OF THE INVENTION

According to a first aspect of the present invention, a self-contained, patient-fillable ampule for a jet injector includes an elongate ampule body having an injection orifice at a first end, a propellant at a second end, and a hollow portion therebetween, along with a piston slidably and sealingly mounted in the hollow portion of the ampule body, wherein the ampule also includes an auxiliary access opening in the body in proximity to the piston. The term "self-contained ampule" is used herein to mean an ampule containing a propellant, a piston or plunger, a hollow portion or chamber for fluid medicine, and an injection orifice in an ampule body.

According to another aspect of the invention, a self-contained disposable ampule for a jet injector includes an elongate ampule body having an injection orifice at a first end, a propellant at a second end, and a hollow portion therebetween which is internally tapered along its longitudinal axis. The hollow portion has an expandable wall structure. The ampule also includes a plunger slidably and sealingly mounted in the hollow portion of the ampule body.

According to a further aspect of the present invention, a self-contained disposable ampule includes an elongate plastic body with an injection orifice at a first end, an internal propellant at a closed second end, and a piston slidably and sealingly mounted within the body entirely between the orifice and the internal propellant. The ampule side wall structure is such that it requires external support to withstand normal peak operating pressures developed during an injection.

A high-resolution metered filling device constitutes another aspect of the present invention. The filling device comprises a rotary-to-linear filling actuator including a linear drive member threaded to a rotary drive member, and a digital dosage display connected to said actuator and synchronously responsive to the rotary drive member. A drive block and drive screw as disclosed herein constitute one form of linear and rotary drive members, respectively, although other forms are contemplated. The digital dosage display includes a drum bearing a plurality of dosage values in integer form arranged in a spiral pattern on its surface, and a drum cover threadedly connected to the drum with a thread pitch matching the pitch of the spiral pattern. The drum cover extends over the drum and has a dosage selection window therein slightly greater in size than a single integer value and in registry with the spiral pattern, whereby a single dosage value is visible at a time through the window during rotation of the drum relative to the window.

It is a general object of the present invention to provide an improved hypodermic jet injector.

Another object of the invention is to provide a hypodermic jet injector with an improved type of disposable ampule.

Another object of the invention is to provide a hypodermic jet injector which includes a filling mechanism in a single unit.

A further object is to provide a filling mechanism that is fast and simple for untrained or vision-impaired individuals to use without sacrificing measurement precision.

These and other objects and advantages of the present invention will become more apparent upon reading the following detailed description of the preferred embodiment in conjunction with the accompanying drawings.

BRIEF DESCRIPTION OF THE DRAWINGS

FIG. 3 is an exploded left side view of an ampule according to the present invention.

FIG. 4 is a cross-sectional side view of the FIG. 3 ampule within an ampule chamber according to the present invention.

FIG. 8 is a perspective view of the multi-purpose parallelogram assembly shown in FIG. 2.

FIGS. 9A and 9B are schematic illustrations of the parallelogram assembly in two operating positions.

FIG. 14 is a perspective view of the firing pin and mounting block along with the associated spring support link and cam follower.

DESCRIPTION OF THE PREFERRED EMBODIMENT

Figure 1:
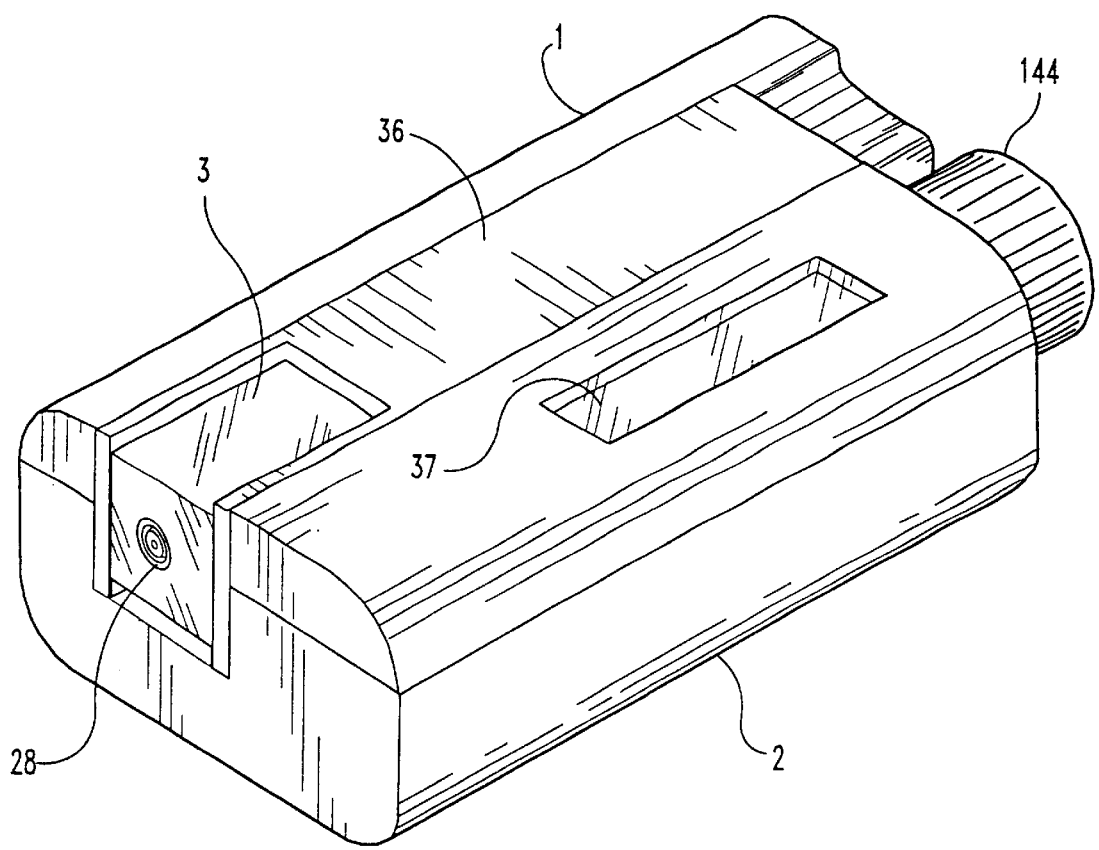
FIG. 1 is a perspective view of a hypodermic jet injector with internal filling mechanism according to a first embodiment of the invention.

For the purposes of promoting an understanding of the principles of the invention, reference will now be made to the embodiment illustrated in the drawings and specific language will be used to describe the same. It will nevertheless be understood that no limitation of the scope of the invention is thereby intended, such alterations and further modifications in the illustrated device, and such further applications of the principles of the invention as illustrated therein being contemplated as would normally occur to one skilled in the art to which the invention relates.

Figure 2:
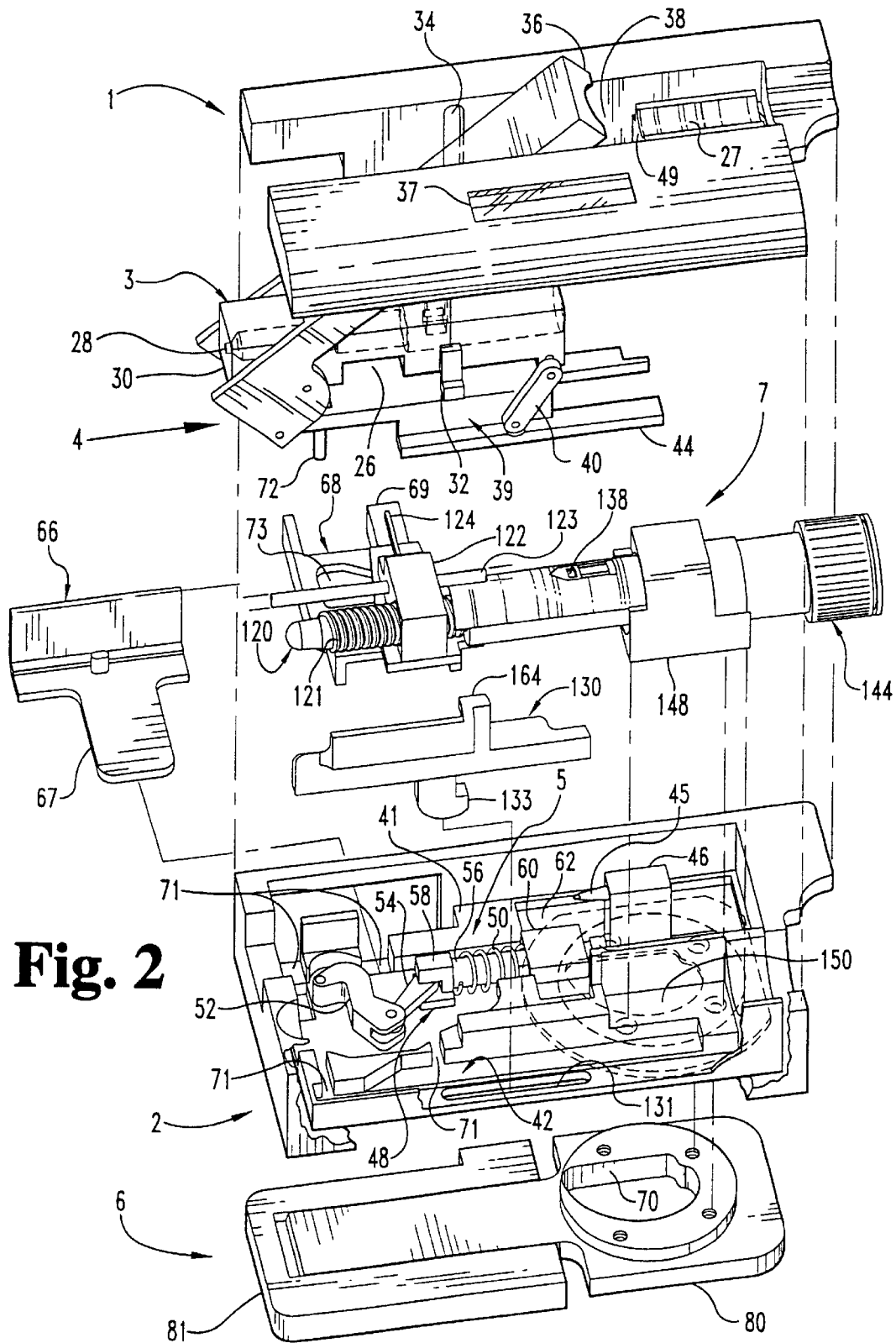
FIG. 2 is an exploded perspective view of the jet injector of FIG. 1.

With reference to FIGS. 1 and 2, a first embodiment of a jet injector according to the present invention includes a housing having a top case 1 and bottom case 2 which together enclose an ampule chamber 3 and associated multifunction assembly 4, a trigger assembly 5, an extendable cocking lever 6, and a metered filling mechanism 7. Briefly described, the injector is designed to receive and fill a self-contained, disposable ampule having a piston which is externally accessible, preferably through the ampule side wall. The trigger assembly is cocked by extending and rotating the cocking lever 6 and then lifting the handle 36 on assembly 4. The latter action also raises the ampule chamber for loading and resets the trigger to the firing position for the next injection. An empty ampule is loaded into the ampule chamber and then the handle is lowered to return the ampule chamber to its original position in order to fill the ampule. The cocking lever is rotated back to its forward position and its extension is used as a platform for securely attaching a medicine vial and adapter to the front end of the ampule. The filling mechanism is then operated to engage and move the ampule piston rearwardly to draw fluid medicine into the ampule through its injection orifice, after which the vial and adapter are removed. The filling mechanism is automatically disengaged from the ampule and an injection is given, in sequence, by actuating the trigger assembly with the injector in contact with a patient's skin.

More specifically, the ampule chamber is designed to receive and support a self-contained, disposable, thin-walled ampule 10 having, as shown in FIGS. 3 and 4, an explosive charge 12 at the rear end 14 thereof, an injection orifice 16 at its front end 18, a double piston 20 and a fluid medicine chamber 22, and further having an access opening 24 for access to the piston for the purpose of filling the ampule after it is loaded into the ampule chamber, as will be described. The ampule chamber is provided with a corresponding access opening 26 in its side and bottom walls. Loading of an ampule into the ampule chamber is facilitated by a guide channel 27 located on the top case to the rear of the ampule chamber and aligned with the inside surface of the ampule chamber in its raised (loading) position. The ampule chamber has an opening 28 approximately 0.25" in diameter in the center of its front end 30 which mates with the tip 17 of the ampule such that the front surface of the ampule tip is flush with the front surface of the ampule chamber. Thus, medicine may be discharged through the ampule orifice and directly into the skin of a patient against which the jet injector is held for an injection.

The ampule chamber is attached to the top case by a pair of integral guide tabs or keys 32 formed to fit into slots 34 in the top case, whereby the ampule chamber is constrained to vertical motion. The ampule chamber is raised for loading and lowered for filling and for injection, as alluded to above, by means of handle 36, which fits through an opening 38 in the top case. The handle has a hollow underside permitting parallel contact with the top of the ampule chamber when in the lowered position, as shown in FIG. 1. A recess is provided on either side of guide channel 27 to receive the sides of the end of the handle for this purpose.

Handle 36 forms part of multifunction parallelogram assembly 4, shown in further detail in FIG. 8. The ampule chamber and a horizontal slider 39 constitute the top and bottom segments of the parallelogram, respectively, and they are interconnected by the loading handle and by a pair of rear links 40. The horizontal slider is limited to horizontal motion by constraints in the case, i.e., by a pair of horizontal surfaces 41 and a pair of horizontal surfaces 43 (FIG. 9) in sliding contact with the top and bottom surfaces, respectively, of a pair of legs 44 on slider 39. Surfaces 41 are formed on a base 42 which is fastened to the bottom case; surfaces 43 are the bottom surfaces of the sidewalls defining the opening 38 in the top case. The horizontal and vertical constraints and the corresponding action of the parallelogram assembly can perhaps be better appreciated from FIGS. 9A and 9B, which schematically illustrate the parallelogram assembly in its two operating positions. FIG. 9A illustrates the position of the assembly with loading handle 36 down, which is the proper position for filling and firing as well as when the injector is not in use. FIG. 9B illustrates the assembly in its position with the loading handle up, which is the proper position for loading an ampule into the ampule chamber and for completion of the cocking sequence.

The trigger assembly is mounted on base 42 in the bottom case, and it includes a firing pin 45 affixed by a conical rear portion thereof to a mounting block 46 connected to a horizontally movable spring linkage 48 which is biased forward by means of a compression spring 50 so as to cause the firing pin to move rapidly toward the charge at the rear end of the ampule when the injector is triggered. A space is provided in the top case under guide channel 27 for mounting block 46, and a wall 49 is provided under the forward end of the guide channel as a rear support for the ampule chamber when the injector is triggered. The wall is provided with a hole to allow passage of the firing pin.

With combined reference to FIGS. 2 and 6, the spring linkage consists of two pivot links 52 and 54 and a spring support link 56 affixed to firing pin mounting block 46. Compression spring 50 is mounted on support link 56 and extends between a pivot block 58 on the front end of the support link and a stop 60 on a plate 62 which holds the linkage in place on the base in the bottom case. The forward pivot point 64 of forward link 52 is fixed to the base by a pivot pin and associated hole in the base. A trigger button 66 is slidably mounted by means of a tongue 67 between the bottom case and base 42 in a guideway formed in the bottom case for this purpose. The trigger button is connected to a button slider 68 which is slidably mounted on base 42 by means of a set of guide rails 69 and mating guide channels 71. One of the guide rails on the button slider comes into contact with and moves forward link 52 when the trigger is pressed, and thereby releases the compression spring which then drives the firing pin forward, as will be explained.

The jet injector employs a two-stage cocking mechanism which includes the cocking lever and an associated cam 70, as well as a vertical pin 72 descending from horizontal slider 39 through a hole 73 in the button slider to a position in front of the spring linkage. Cam 70 is integrally formed within the main portion 80 of the cocking lever, which is horizontally rotatably mounted in the bottom case. A cam follower 74 is mounted on the bottom of the firing pin mounting block 46 at the level of the cam and is held in contact with the cam by spring 50. A longitudinal slot 76 (FIG. 6A), corresponding in length to the stroke length of the firing pin, is provided in base 42 for connection of the firing pin mounting block to cam follower 74, which preferably includes a roller 78 for low-friction contact with the cam surface. A telescopic extension 81, which may be spring-biased toward its retracted position, is provided on the cocking lever for increased leverage during cocking and also as a platform for a vial and filling adapter, as will be described in connection with the filling mechanism.

Figure 6A:
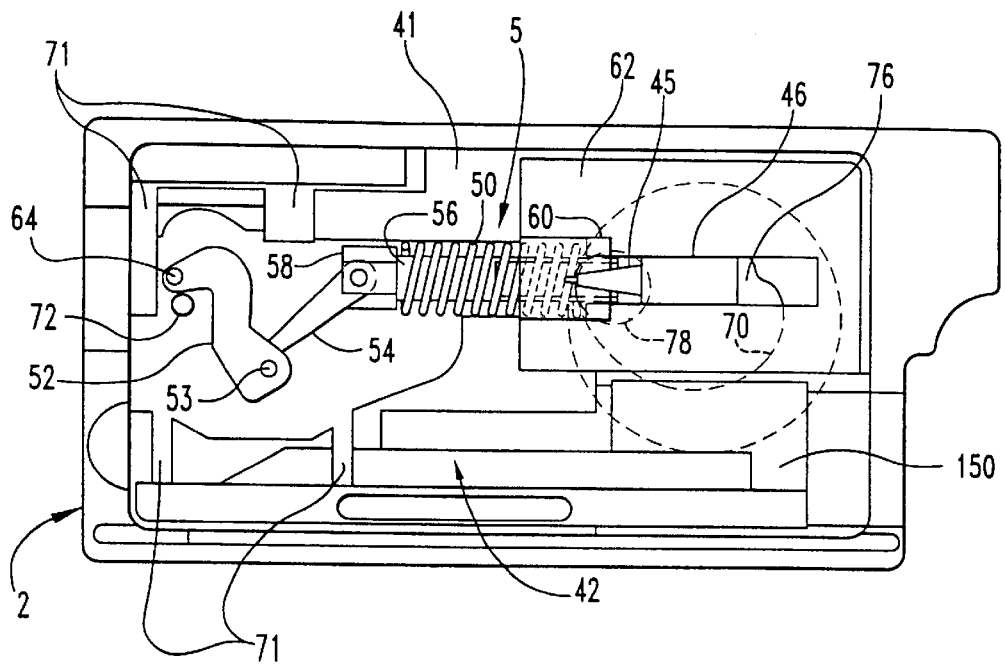
FIGS. 6A, B and C are top views of the bottom case of the jet injector housing with the trigger assembly in different positions.

FIGS. 6A, B and C illustrate the trigger mechanism in its released, semi-cocked and fully cocked positions, respectively, along with pertinent portions of the cocking mechanism including the vertical pin on the bottom of the horizontal slider. The trigger button and other parts of the injector are removed for ease of illustration. With the cocking lever in its resting position, shown in FIG. 2, the cam follower 74 is at its forwardmost position, as determined by the shape of cam 70, and the spring linkage and firing pin are correspondingly in their forwardmost position as illustrated in FIG. 6A.

FIG. 6B illustrates the trigger mechanism with the cocking lever rotated 180° clockwise, as viewed from above. By rotation of the cocking lever, and correspondingly the cam, to this position, the firing pin and linkage are pulled back against the force of the spring to the position shown. It will be appreciated by those skilled in the art that this semi-cocked position of the spring linkage is unstable in that the spring force will be immediately released upon return of the cocking lever to its original position.

However, as shown in FIG. 6C, the trigger mechanism is placed in a stable, fully cocked position by rearward motion of pin 72 into contact with link 52 while the cocking lever is still in its outer position. The pin is moved by lifting handle 36 on the parallelogram assembly, which causes slider 39 to slide back in the housing. Pin 72 thereby forces link 52 to pivot counterclockwise until the pivot pin 53 interconnecting links 52 and 54 crosses the center line of the spring linkage, at which point the spring causes the linkage to snap into the position shown in FIG. 6C. The linkage is restrained by the adjacent wall of base 42, as illustrated, and remains stationary in that position after the cocking lever is returned to its original position and until the trigger is pressed to fire the device.

Figure 7:
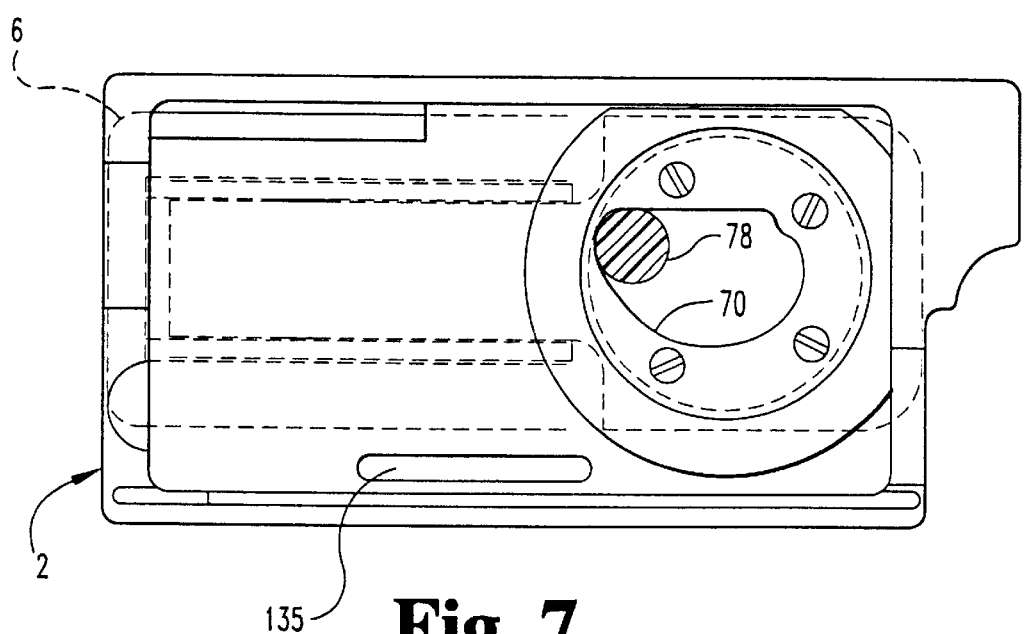
FIG. 7 is a top view of the bottom case illustrating the presently preferred cam shape for use in conjunction with the jet injector of FIGS. 1 and 2.

The cam shape illustrated in FIGS. 2 and 6 and shown particularly clearly in FIG. 7 has been determined to provide an increasing mechanical advantage during rotation of the cocking lever, thereby compensating for increasing spring resistance during spring compression and also for angle-dependent changes in components of spring force and friction during rotation of the lever. As a result, the force required to rotate the lever rises initially with displacement but substantially levels off and thereby provides a more even feel for a user cocking the trigger mechanism.

The preferred embodiment of a disposable ampule according to the present invention includes a double piston, as mentioned above. The ampule piston is referred to as a double piston because it includes two plungers or seals interconnected by a connecting rod. The connecting rod is sized and shaped to provide an air space extending between the two seals. This double piston construction, in conjunction with the access openings in the walls of the ampule and ampule chamber, serves two purposes: 1) it enables a mechanical arm or other engagement member to access, engage and move the piston and thereby draw fluid medicine into the ampule; and 2) it prevents contamination of the medicine during the filing process by means of a vent to the outside atmosphere from a space between the medicine chamber and the combustion chamber within the ampule. The medicine chamber and combustion chamber both experience high pressures during an injection, whereas the space around the connecting rod between the front and rear seals is at atmospheric pressure. Should any combustion gases leak past the rear seal, they would be vented to the atmosphere through access opening 24 in the ampule and access opening 26 in the ampule chamber and would not be able to mix with any medicine in the medicine chamber. This is because it is impossible for gases to travel against a pressure gradient into the medicine chamber.

Figure 5:
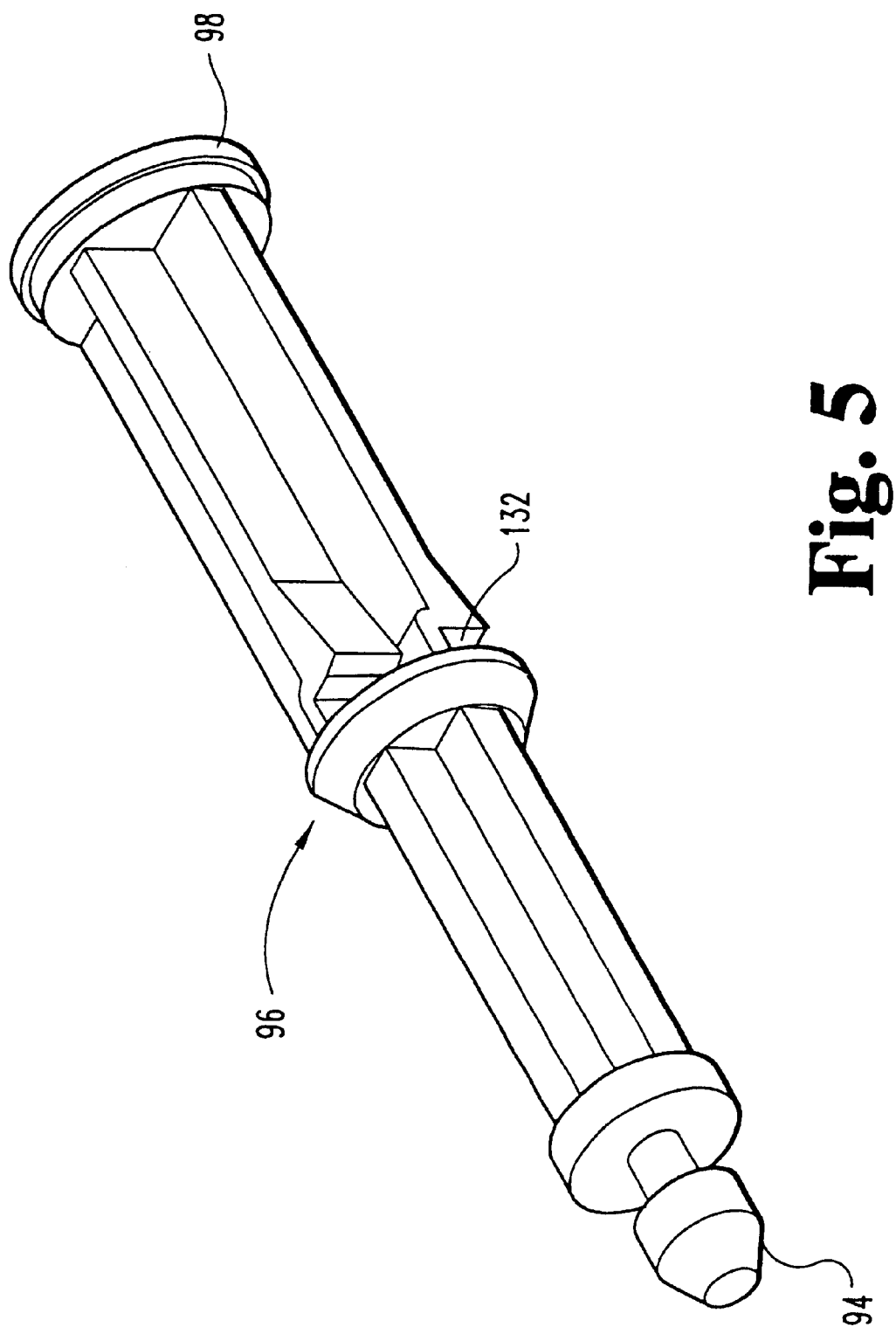
FIG. 5 is a perspective view of the combination connecting rod and rear seal of the double piston shown in FIGS. 3 and 4.

Disposable ampule 10 is disclosed in further detail in FIGS. 3–5, from which it can be seen that the ampule has a main body 90 in which the double piston 20 is slidably and sealingly mounted, with the double piston having a plunger 92 snapped on the front end 94 of an integrally molded combination of a connecting rod 96 and rear seal 98. Preferably, the plunger is soft rubber and the connecting rod and rear seal are relatively hard and non-compressible. The connecting rod is preferably formed with two spaced sets of four elongated ribs as shown in FIG. 5, for purposes of a low-cost substantially rigid construction and large vent passageways. The rear end 14 of the ampule is closed by a piston stop and primer support 100 which is press fitted into the rear end of main body 90, as shown in FIG. 4, by primer 12 and by a primer holder 102 press fitted over the rear of piston stop 100. Piston stop 100 is hollow and includes a seat 104 in its rear end which cooperates with a cup 106 in the rear of primer holder 102 to hold primer 12 which is preferably a Winchester large rifle primer, which contains approximately 350 mg of azide. The primer cap is exposed to the rear by an access hole 107, which the firing pin enters to engage and mechanically actuate the primer cap. The conical rear portion of the firing pin and the access hole cooperate to ensure that the firing pin is centered when it engages the primer cap, and also to maintain a seal at the rear end of the ampule during detonation of the charge.

An opaque sleeve 108 is provided to cover the portion of the main ampule body 90 to the rear of access opening 24 as well as the piston stop and primer holder as shown in FIG. 4. A thin gap 109 approximately 0.010" is provided between the sleeve and the central portion of the ampule body to allow for expansion of the ampule body to facilitate forward motion of the piston during an injection. The main ampule body, the sleeve, the connecting rod and rear seal, the piston stop and primer holder are all preferably formed of polypropylene or other inexpensive plastic material. The main ampule body is preferably formed of a transparent polypropylene, with sidewalls preferably in the range of 0.025–0.040" for medicine chamber 22 and combustion chamber 110, with an average wall thickness of 0.030". Alternatively, the ampule may be constructed of high density polyethylene. Front end 18 is tapered and sized so as to fit in the approximately 0.25" diameter opening in the front end of the ampule chamber. The ampule body defines tapered surfaces 112 and. 114 which lead from the injection orifice 16, which preferably has a diameter of 0.005", to medicine chamber 22. The ampule sleeve is preferably opaque so as to obscure the view of the combustion chamber in the ampule which may become unsightly after discharge due to soot or other residue from the primer discharge. Rear seal 98 may be a polypropylene disk of sufficient hardness and axial thickness, preferably approximately 0.030" or more, to be substantially non-compressible, whereas the main body of the ampule is readily expandable and requires external support to withstand the normal operating pressures developed within it during an injection. Alternatively, a hard Velbron or butadiene rubber may be employed for the rear seal. The ampule main body is preferably molded with draft angles on the interior and exterior surfaces of its front and rear chambers as well as its central section, for more efficient injection molding. The interior surfaces preferably have a draft angle of approximately 0.25°, and the exterior surfaces preferably have a draft angle of approximately 0.5–1.0°. The ampule construction as described above offers significant advantages including lower cost due to less material and shorter molding cycle times, as well as greater ease of manufacturing due to the use of draft angles.

The ampule chamber is molded from a strong, high-grade, transparent plastic such as polycarbonate, and has a draft angle on the front chamber section to match the draft angle on the front section of the ampule. A draft angle is suitable in this section of the ampule chamber because the soft rubber plunger inside the ampule will compress as it moves forward during an injection. The rear section of the ampule chamber is provided with a straight bore to provide expansion space for the ampule to "balloon out" as the harder, non-compressible rear seal is forced forward through the decreasing diameter of the thin-walled ampule. The central section of the ampule chamber may also have a straight bore, although a draft angle on that section may be suitable in some applications. With straight bores in the central and rear sections of the ampule chamber, and with draft angles on the ampule as indicated above, gaps of approximately 0.010" are obtained at points A and B, respectively, in FIG. 4 (draft angles slightly exaggerated for illustration of the gaps).

Access opening 24 in the ampule preferably extends approximately 90° circumferentially around main body 90, and is designed to be oriented as shown in FIG. 3 when loaded into the ampule chamber, whereby the access openings in the ampule and ampule chamber are aligned for filling purposes. For this purpose, sleeve 108 is provided with a key 116 approximately 0.200–0.250" in length and of suitable width and is precisely attached to the main body of the ampule such that key 116 is in line with the bottom edge of opening 24. A mating slot 118 is provided in the ampule chamber at the bottom rear end of the bore therein. Thus, an empty ampule can be readily loaded into the ampule chamber with the proper orientation. The double piston is preferably installed in its forwardmost position in the ampule, corresponding to a zero dosage, and oriented with the ribs on the connecting rod in horizontal and vertical planes as shown in FIG. 4.

An annular groove 19 with square edges as shown in FIG. 4 is formed in the tip of the ampule for filling purposes, and, more specifically, to facilitate a sealed connection to a filling adapter having a mating annular protrusion with a slightly oversize curved surface designed for primary contact with the outer corners of the groove. An outlet orifice is provided in the center of the annular protrusion in communication with a needle adapted to penetrate the septum of a medicine vial pressed against the other end of the adapter. A second needle, different in length from the first, may be included in the adapter to provide a vent for the medicine vial to reduce the pressure required for medicine withdrawal. The needle lengths should be sufficiently different that one needle tip can be positioned near the top of the medicine vial with the other tip near the bottom of the vial. A support adapted for mounting on extension 81 of the cocking lever is provided to firmly hold the medicine vial and adapter together and maintain a seal between the adapter and ampule. Preferably, spring loading is provided for these purposes, by means of a spring-loaded extension on the cocking lever and/or spring loading in the support for the vial and adapter.

Figure 12:
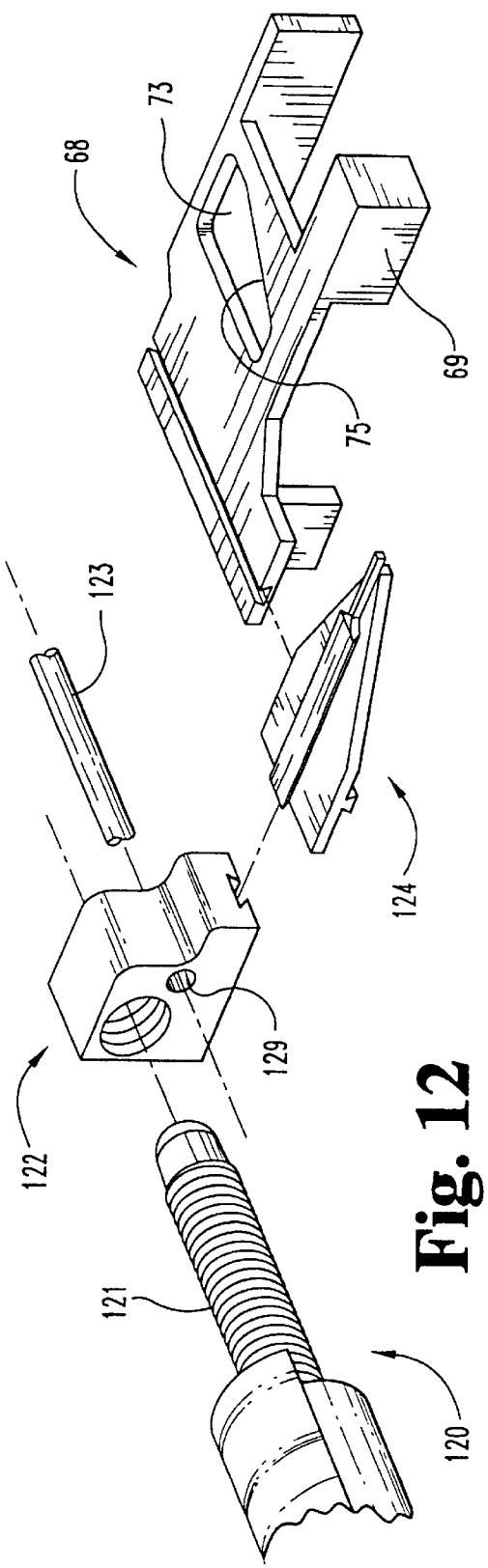
FIG. 12 is an exploded perspective view of another portion of the metered filling mechanism.

As shown in detail in FIG. 12, the metered filling mechanism 7 includes a rotatably mounted drive screw 120 the front end 121 of which is threadedly attached to a drive block 122 which is in turn slidably connected to a guide rod 123 and to a piston connecting pin 124, which is the preferred form of piston engagement member. Pin 124 is in turn slidably connected to button slider 68, which is connected to the trigger button and slidably mounted on base 42 by mating guide rails and channels, as described earlier. The drive block, piston connecting pin and button slider are interconnected by dovetail slots and rails as shown in FIG. 12, whereby the connecting pin moves axially with the drive block when the drive screw is turned, sliding upon the button slider at this time, and is also free to move laterally with the button slider, sliding under the drive block at this time. The button slider moves and carries the connecting pin toward the ampule during the cocking process, primarily in response to the motion of pivot link 52 and, if desired, also in response to vertical pin 72 contacting an optional angled surface 75 of hole 73. The button slider carries the connecting pin away from the ampule when the injector is triggered. Guide rod 123 is provided to reduce play due to tolerancing. It is slidably mounted in an unthreaded hole 129 in the drive block and supported on each end by the top case, with the rear end of the rod mounted in a vertical wall or bracket formed in the top case and the front end mounted in the front wall of the top case. A through-hole may be provided in the front hole of the top case for insertion of the guide rod to facilitate assembly of the injector.

Figure 10:
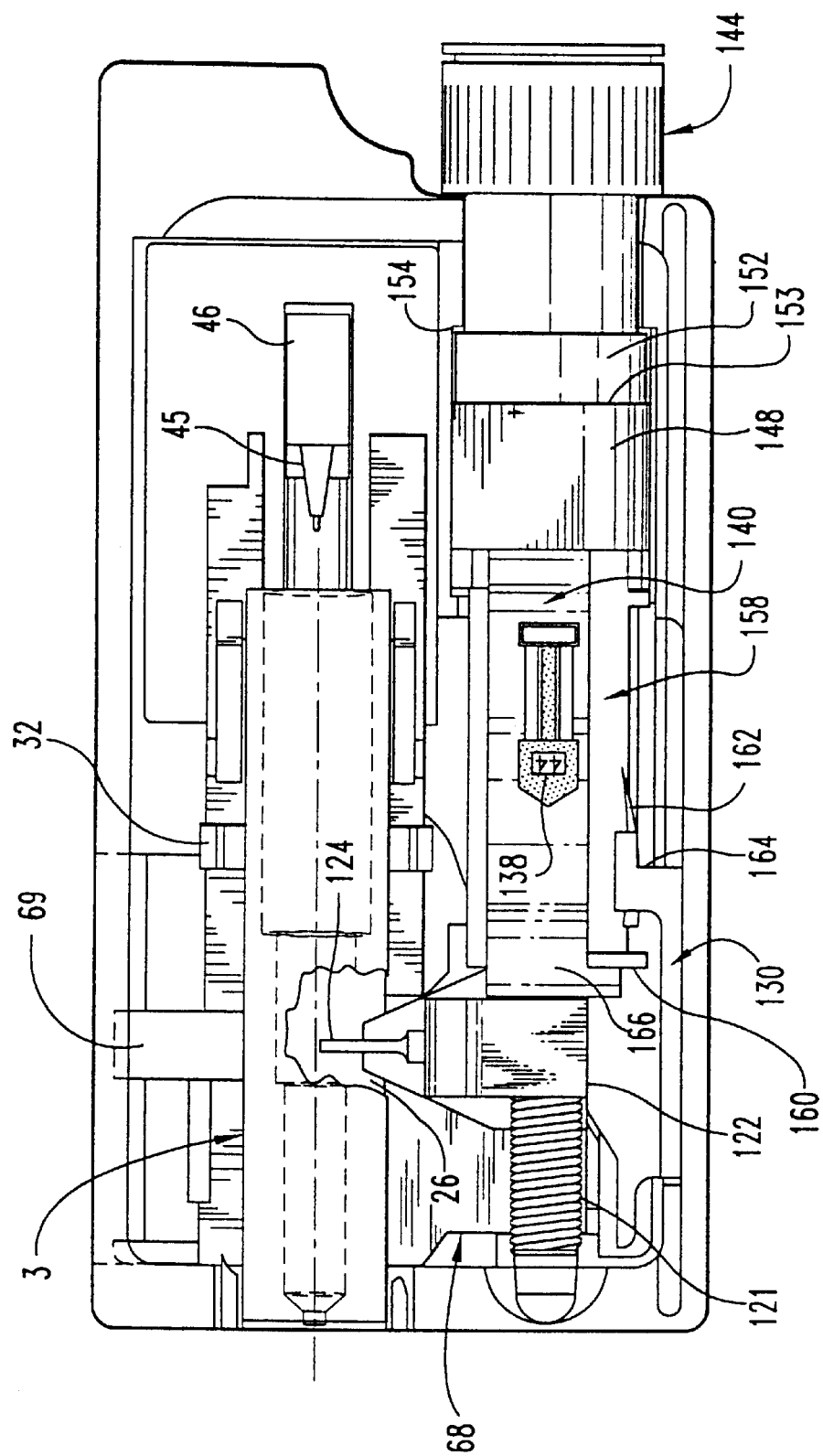
FIG. 10 is a top view of the bottom case of the jet injector housing illustrating the metered filling mechanism in conjunction with the ampule chamber.
Figure 13:
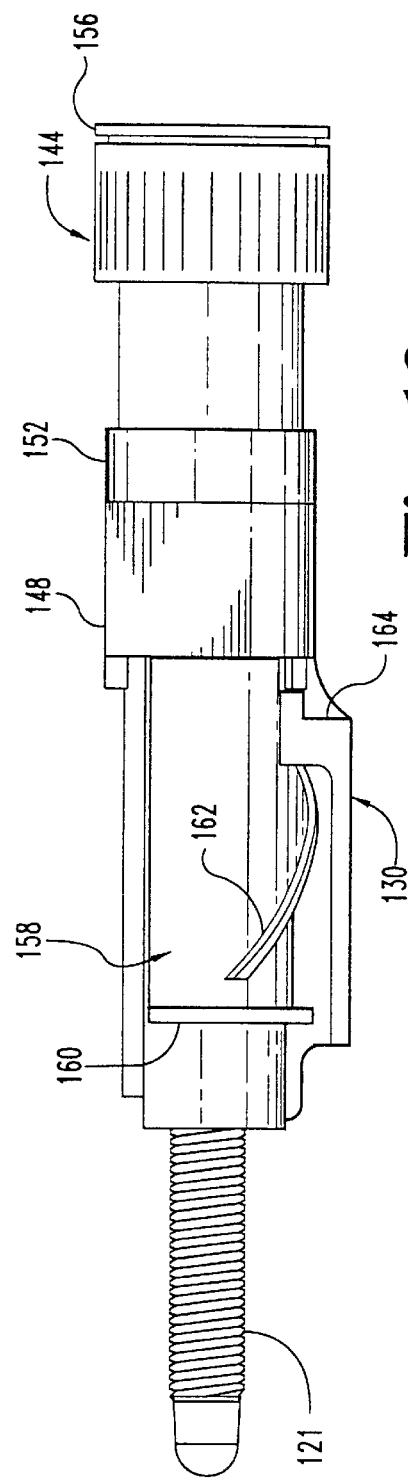
FIG. 13 is a top view of a portion of the metered filling mechanism.

Referring to FIGS. 10 and 13 in addition to FIG. 2, a button lock 130 is provided as a safety lock for the trigger, and also for the purpose of moving the piston connecting pin into position for engagement with the double piston in an ampule lowered into position for filling. The button lock slides axially in a guide channel 131 provided in base 42 for this purpose, and its axial position is controlled from underneath the housing by a thumb tab 133 extending down from the button lock through a slot 135 (FIG. 7) in the bottom case.

Piston connecting pin 124 is sized and shaped to snugly fit within a slot 132 (FIGS. 4 and 5) formed within the connecting rod of the piston for this purpose, and desirably includes a tapered upper surface to compensate for potential misalignments with respect to the slot in the connecting rod. It is preferably set at the zero position (zero dosage) before an ampule is lowered onto it and, as mentioned above, the ampule piston is correspondingly set at the zero position. With the connecting pin in its extended position, shown in FIG. 10, and with the pin in engagement with the connecting rod of an ampule loaded in the ampule chamber, the ampule can be filled by turning the drive screw to move the drive block rearwardly and thereby move the ampule piston back the same distance. The motion of the piston within the ampule causes medicine to be drawn through the ampule orifice from a medicine vial to which the jet injector is attached for this purpose via a suitable adapter such as described above.

Figure 11:
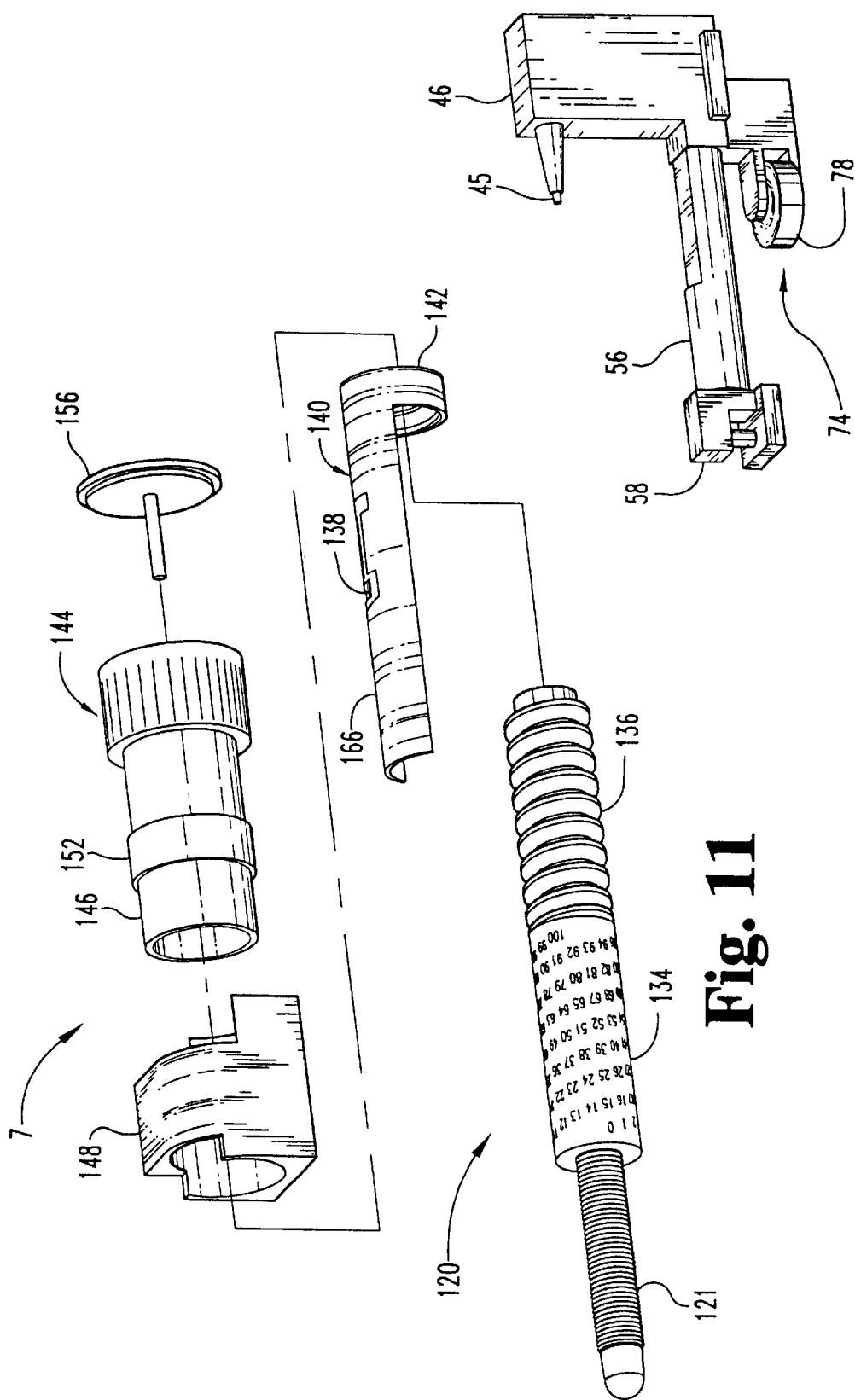
FIG. 11 is an exploded perspective view of a portion of the metered filling mechanism.

The drive screw has relatively fine threads on its front end for engagement with the drive block, which is provided with matching threads, and also includes a number drum 134 and a section 136 of coarse threads to the rear thereof, as shown in detail in FIG. 11. The number drum bears numerical dosage values in a spiral arrangement conforming to the spiral shape of the coarse threads on the rear end of the drive screw. A dosage selection window 138 is provided in a drum cover 140 which is mounted over the number drum and moved axially with respect thereto by an internally threaded ring 142 which engages the coarse threads 136 on the drive screw. The rear end of the drive screw is rotatably fixed with respect to a rotatable metering knob 144 such that it rotates with the knob. The forward end 146 of the metering knob is rotatably mounted within a support block 148 which is retained in base 42 in a recess 150 adapted to mate with the bottom of the support block so as to prevent any horizontal motion thereof. As shown in more detail in FIG. 10, a shoulder 152 on the metering knob is positioned between the upper rear surface 153 of support block 148 and the rear end wall 154 of recess 150, thereby fixing the metering knob axially with respect to the case. Drum cover 140 is keyed to support block 148 so as to limit the drum cover to axial motion with respect to the case. A calibration screw 156 is rotatably mounted on the rear of and axially fixed with respect to the metering knob and threadedly engages the interior of the rear end of the drive screw, whereby rotation of the calibration screw causes axial motion of the drive screw for purposes of minor calibration adjustments.

Window 138 is covered by a shade 158 when button lock 130 is in its unlocked position, which is illustrated in FIG. 13, such that the dosage value is not visible to a user at such times. Window shade 158 is axially fixed with respect to the case by a flange 160 and by a corresponding surface formed in the upper case for this purpose. A helical rib 162 on the shade and a mating slot on the inside surface of upper portion 164 of the button lock cooperate to rotate the shade when the button lock is moved axially. As shown in FIG. 10, when the button lock is moved forwardly to its locked position, the proper position for filling the ampule, the shade is rotated away from the window and the dosage value is visible to the user. The user can also see, through window 37 in the top case, the forward surface 166 of drum cover 140, and forward surface 166 is preferably colored blue or another appropriate color to present the appearance of fluid medicine in a syringe and thereby provide a user with additional visual feedback on a filling operation in process. Of course, with a transparent ampule chamber and ampule as described above, the actual medicine content of an ampule is visible, along with any air bubbles that may be present, through the front section of the ampule chamber as can readily be appreciated from FIG. 1.

However, the primary display is by means of the dosage selection window, which presents the user with the precise dosage value, preferably within a range of 0 to 100 units of medicine, and with one number visible at a time to eliminate confusion. Smaller and larger ranges are also contemplated for particular applications, as are different units of measure.

The number drum as described above provides a high resolution digital display, by which is meant a display of values in integer form, in a limited space. The numbers are placed along a spiral path on the number drum that matches the pitch of the coarse threads on the drive screw. The difference in pitch between the fine and coarse threads on the drive screw provides a mechanical scale factor which results in a high resolution digital readout of up to 100 units of insulin, for example, with less than 10 turns of the metering knob. Another advantage of the metering device according to the present invention is that it makes possible a nonlinear display, which is particularly desirable where, as here, the inside diameter of the ampule varies along its length. The distance between consecutive numbers on number drum 134 is mathematically calculated according to the interior ampule geometry. More specifically, the spacing between high dosage values is less than that for low dosage values because the ampule diameter increases with distance from the tip in the preferred embodiment.

The button lock is moved to its unlocked position (FIG. 13) after filling, when the user desires to give an injection. The injector is then ready for firing. When the trigger button is pressed, it moves the button slider and thereby moves the piston connecting pin out of engagement with the piston, and then, as part of the same continuous motion, forces pivot pin 53 across the center line of the spring linkage and thereby releases the compression spring, which then drives the firing pin into contact with the charge in the ampule, causing detonation which drives the piston forward to force the medicine out of the injector. The above sequential motion is important in order to ensure that the filling mechanism does not inhibit piston motion within an ampule during an injection. For this purpose, the button slider guide rail which contacts the pivot link 52 in the trigger assembly is preferably dimensioned such that there is a gap of approximately 0.100–0.125" between it and pivot link 52 when it is in the filling position.

Figure 15:
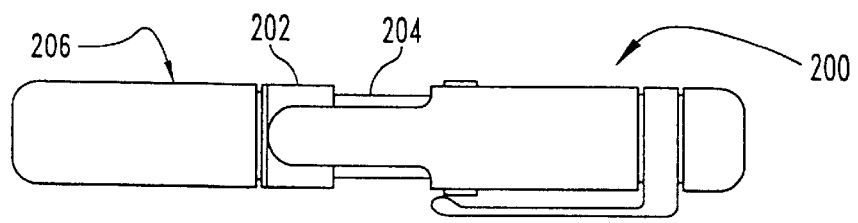
FIG. 15 is a side view of a hypodermic jet injector according to a second embodiment of the invention.
Figure 16:
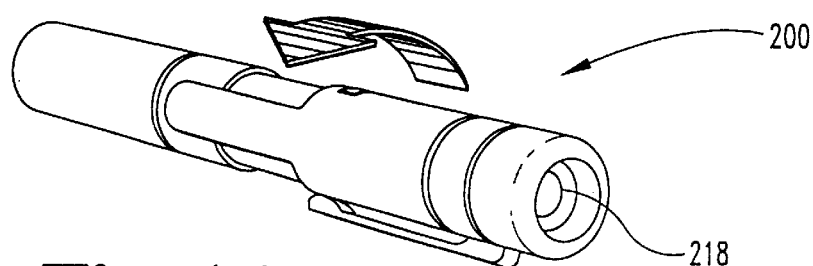
FIG. 16 is a perspective view of the hypodermic jet injector of FIG. 15.
Figure 17:
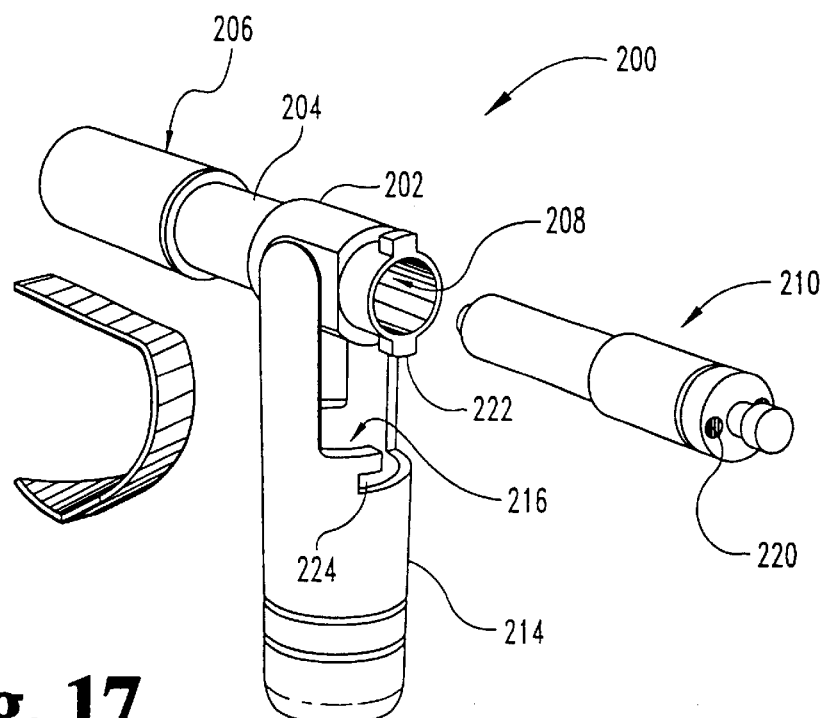
FIG. 17 is a perspective view of the hypodermic jet injector of FIGS. 15 and 16 in its open position with an exposed ampule.

In an alternative embodiment shown in FIGS. 15–17, a hypodermic jet injector 200 according to the present invention includes a twist-lock breech. The injector is provided with a slider ring 202 slidably mounted on a relatively narrow portion 204 of a main body 206 of the jet injector. The main body includes a barrel 208 adapted to receive an ampule 210 having generally cylindrical side wall surfaces generally conforming to mating inner surfaces of the barrel extending longitudinally through the main body.

Slider ring 202 is slidably and rotatably mounted on portion 204, and is pivotally connected to a rear body 214 which is provided with a battery compartment 216, a recessed ignition button 218, along with interconnecting electrical conductors arranged to create an electrical circuit for supplying current to an electrical squib in the ampule via contacts 220, as will be described. The main body of the injector unit is provided with a pair of locking pins 222 sized and shaped and positioned to fit securely in a pair of corresponding slots 224 defined in the forward portion of rear body 214, as perhaps best illustrated in FIG. 17.

FIGS. 15–17 illustrate in sequence the operation of opening the injectory unit. From the closed position shown in FIG. 15, the injector is opened by first twisting the main body and rear body relative to each other as illustrated by the arrow in FIG. 16, and then pulling the rear body to the rear and then down, at which point the breech of the barrel is open to receive an ampule. The ampule is sealed in the injector unit by reversing the opening steps to close and lock the injector.

Figure 18:
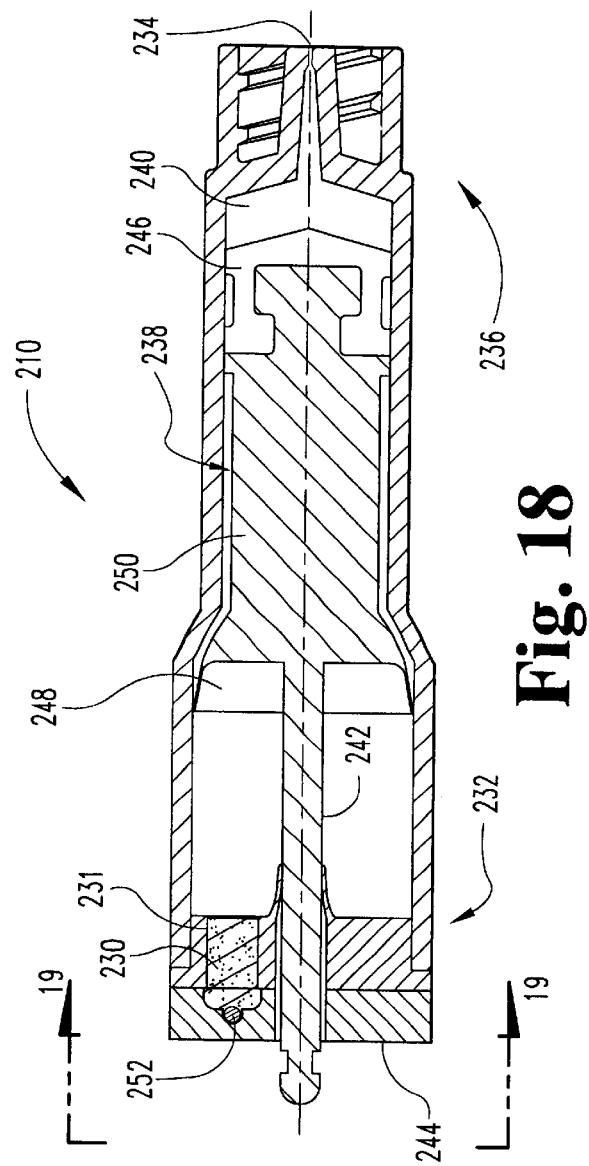
FIG. 18 is a cross-sectional side view of an alternative embodiment of an ampule according to the present invention.
Figure 19:
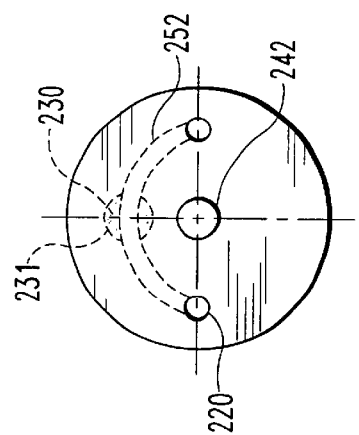
FIG. 19 is an end view of the ampule of FIG. 18.

Details of an ampule construction suitable for use with the injector of FIGS. 15–17 are shown in FIGS. 18 and 19, from which it can be seen that the ampule 210 has an explosive charge 230 contained within chamber 231 at its rear end 232 and an injection orifice 234 at its front end 236, as well as a double piston 238 and a fluid medicine chamber 240. The double piston is accessible from the rear of the ampule by means of a stem or rod 242 extending through the rear wall 244, in which the explosive charge 230 is contained within chamber 231 which is mounted off-center as shown in the drawings. The double piston has a plunger 246 and a rear seal 248 mounted on a connecting rod 250, which is integrally formed with the stem 242, as shown in FIG. 18. As with the ampule of FIG. 3, the ampule side wall structure is preferably such that it requires external support to withstand normal peak operating pressures developed during an injection. A curved electrical conductor 252 is provided between the contacts 220 and passes through the rear part of the chamber for the propellant 230, as shown in FIG. 18, so as to expose the charge to the heat produced by the current flow through the electrical conductor 252 when the electrical circuit is closed to fire the injector. A suitable charge for use with the electrical actuation system just described is a biodegradable powder of the type described in U.S. Pat. No. 4,997,496 to Wehrli, incorporated herein by reference. Propellants of this type have the advantage of being edible and therefore harmless to a patient in the unlikely event that the powder would come into contact with the patient's body after firing.

The stem or rod on the rear end of the ampule is designed for connection to a compatible filling mechanism such that the double plunger can be pulled back to fill the ampule prior to loading into the injector. For this purpose a Luer lock is provided on the front end of the ampule to mate with a correspondingly designed adapter provided with a needle for insertion into a standard medicine vial for purposes of filling the ampule. Dosage indications may be provided on the filling mechanism, or, if desired, may be provided on the side wall structure of the ampule for reading by a user manually pulling on the stem to fill the ampule, as in a standard hypodermic syringe. At least in the latter case, the ampule is preferably transparent.

The contacts 220 may be diametrically opposed as shown in FIGS. 18 and 19 or may be located on a straight line through the powder chamber. In the latter case, a straight electrical conductor is located between the contacts instead of the curved conductor 252 inside the rear wall of the injector.

Figure 20:
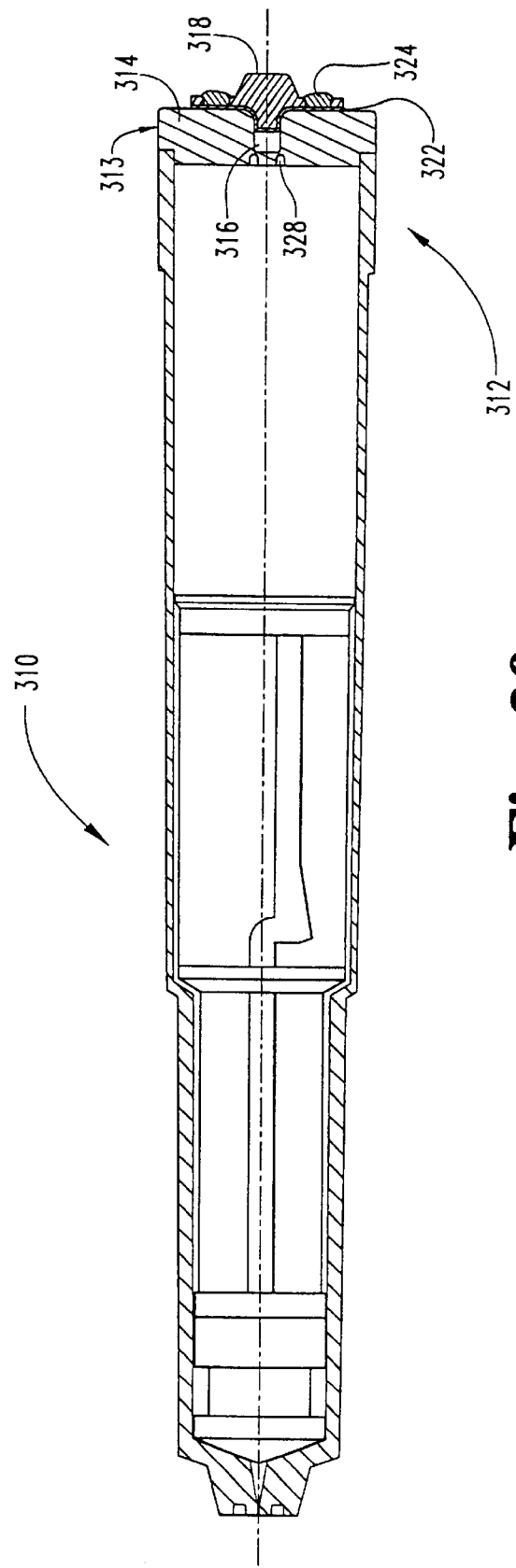
FIG. 20 is a cross-sectional side view of another alternative embodiment of an ampule according to the present invention.
Figure 21:
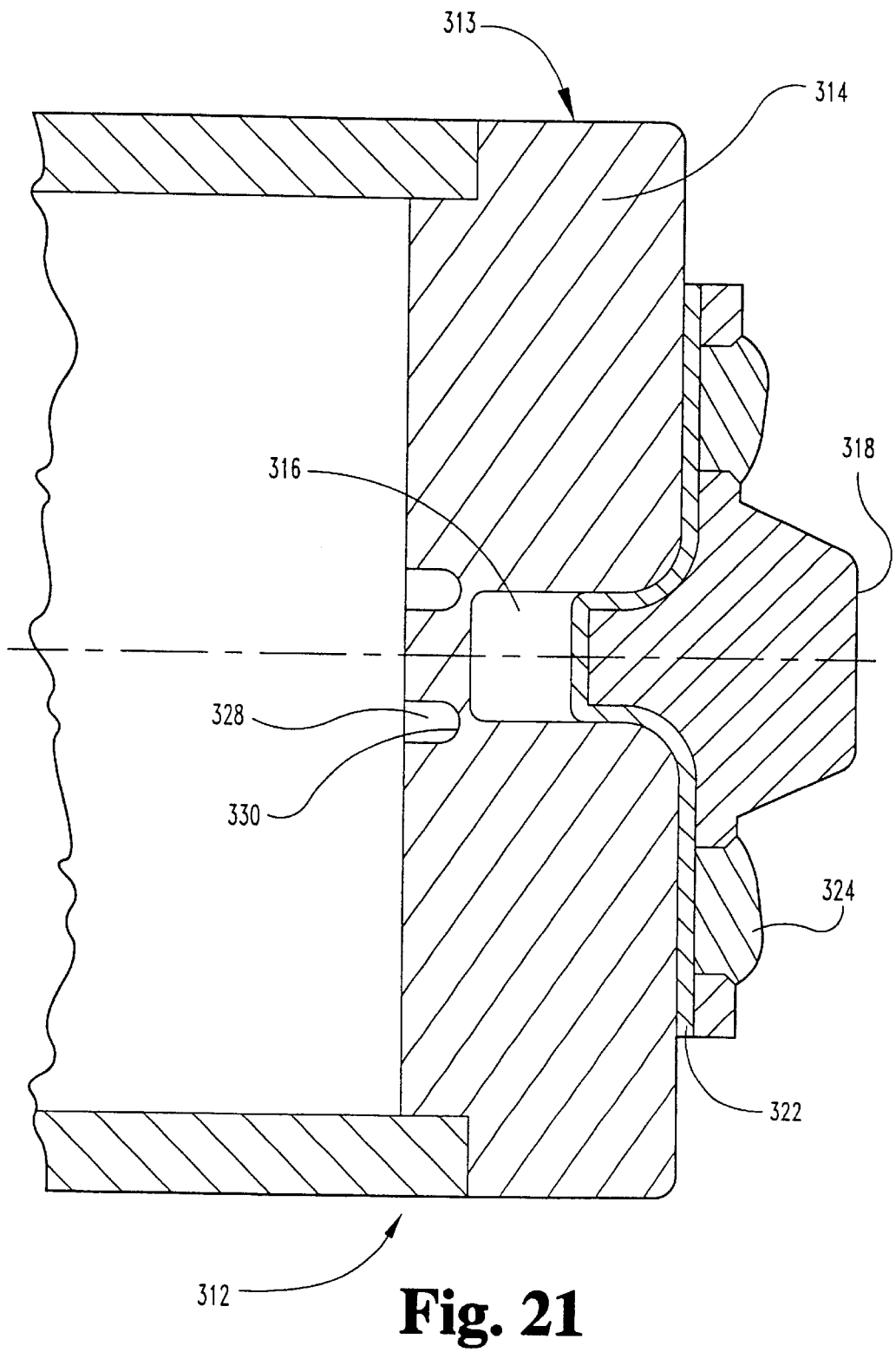
FIG. 21 is a side view of the rear portion of the ampule of FIG. 20.
Figure 22:
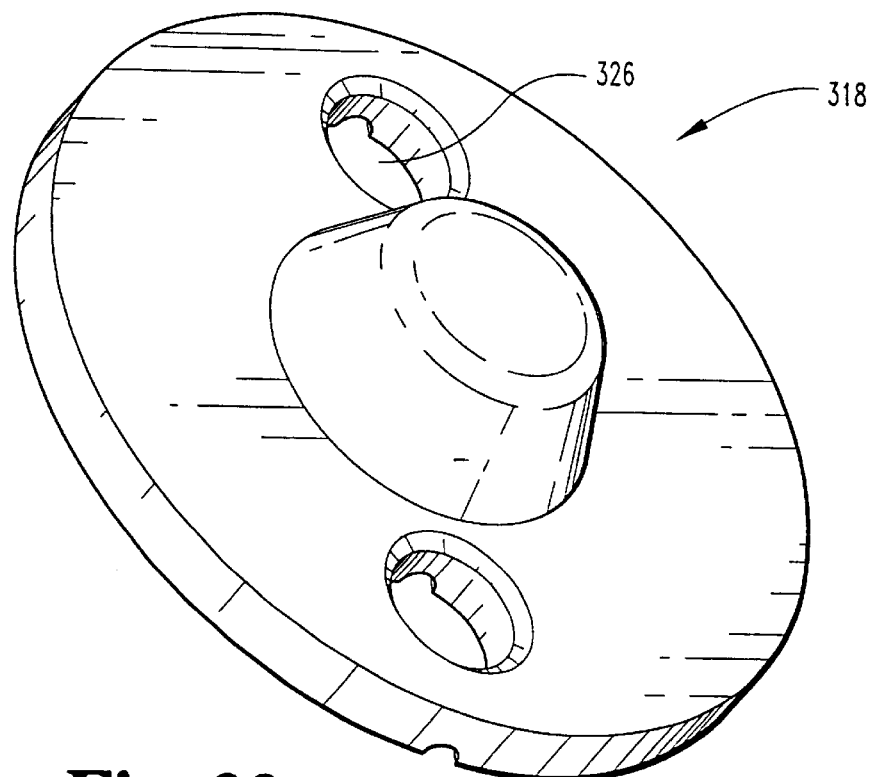
FIG. 22 is a rear perspective view of a rear cap for the ampule of FIG. 20.
Figure 23:
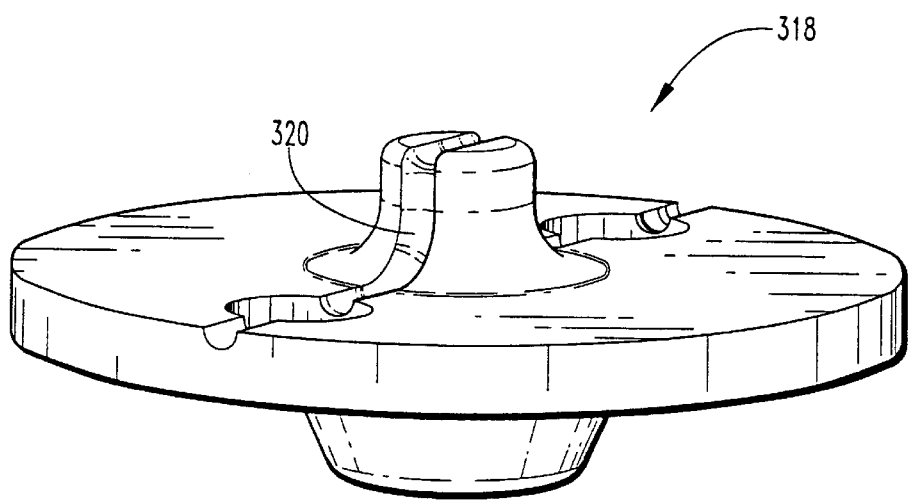
FIG. 23 is a perspective view of the cap of FIG. 22 viewed from a different direction.

An alternative embodiment of an ampule 310 according to the present invention is shown in FIG. 20, wherein it is seen that the side wall structure is the same as that shown in FIG. 3, the principal difference between the two ampules being that, instead of a primer support and primer holder on the rear end 312 of the ampule body, ampule 310 is sealed at the rear by an end cap 313 which includes a cylindrical portion 314 defining a powder chamber 316 which is enclosed by a chamber cap 318. The chamber cap may be ultrasonically welded to end cap 313, which may likewise be ultrasonically welded to the rear end of the ampule side wall. The chamber cap is provided with a slot or groove 320 extending diametrically therethrough to receive a Nichrome wire 322 which, as perhaps best shown in FIG. 21, is exposed to the powder chamber and electrically connected to two solder terminals 324 which are created by providing a pair of solder beads in the exposed holes 326 of the chamber cap. An annular groove 328 is provided in the forward surface of the end cap 313 sufficiently deep to provide a frangible joint 330 between the powder chamber and the groove which is designed to break under the impact of the explosive force when the explosive charge is detonated.

While the invention has been illustrated and described in detail in the drawings and foregoing description, the same is to be considered as illustrative and not restrictive in character, it being understood that only the preferred embodiment has been shown and described and that all changes and modifications that come within the spirit of the invention are desired to be protected. For example, although the disclosed ampule chamber of the first embodiment is especially suited for use with patient-fillable ampules, it is also capable of accommodating prefilled ampules, as is the alternative embodiment of a jet injector. Also, the principles of the high-resolution metered filling device disclosed herein are applicable to independent or integral filling devices designed for connection to the orifice end or opposite end of a jet injector, a hypodermic syringe, a self-contained ampule with or without an auxiliary opening, or other injection devices.

What is claimed is:

1. A self-contained, patient-fillable ampule for a jet injector, comprising:

an elongate ampule body having an injection orifice at a first end, an electrically actuated propellant powder at a second end, and a hollow portion therebetween, said second end having an end wall;

a piston slidably and sealingly mounted in said hollow portion of said ampule body; and a filling control rod coaxial with said hollow portion of said elongate ampule body, said filling control rod connected to said piston and extending through said rear end wall, whereby said ampule may be filled with medicine by a patient by pulling said control rod rearwardly and thereby retracting said piston and drawing medicine in through said injection orifice, and whereby the medicine may be administered by a patient by actuating said electrically actuated propellant powder to propel said piston forward and thereby force the medicine out through said injection orifice.

2. A self-contained, patient-fillable ampule for a jet injector, comprising:

an elongate ampule body having an injection orifice at a first end, a propellant at a second end, and a hollow portion therebetween, said second and having an end wall;

a piston slidably and scalingly mounted in said hollow portion of said ampule body;

a filling control rod coaxial with said hollow portion of said elongate ampule body, said filling control rod connected to said piston and extending through said rear end wall;

whereby said ampule may be filled with medicine by a patient by pulling said control rod rearwardly and thereby retracting said piston and drawing medicine in through said injection orifice, and whereby the medicine may be administered by a patient by actuating said propellant to propel said piston forward and thereby force the medicine out through said injection orifice;

wherein said propellant is electrically actuated; and wherein said piston includes front and rear seals and a connecting rod therebetween, said connecting rod having at least one transverse cross-sectional dimension less than that of said front and rear seals, further comprising a vent in said ampule body adjacent to said connecting rod.

3. The ampule of claim 2, wherein said front seal is softer than said rear seal.

4. The ampule of claim 3, wherein said propellant is an explosive charge.

5. A self-contained, disposable ampule for a jet injector, comprising:

an elongate ampule body having an injection orifice at a first end, an electrically actuated propellant powder at a second end, and a hollow portion therebetween; and a double piston slidably and sealingly mounted in said hollow portion of said ampule body, said double piston including first and second plungers and a connecting rod therebetween.

6. The ampule of claim 5, wherein said hollow portion of said ampule body is plastic with a wall thickness of approximately 0.030".

7. The ampule of claim 6, wherein said first plunger is closer than said second plunger to said first end of said ampule body, said first plunger is compressible, and said second plunger is relatively non-compressible.

8. The ampule of claim 7, further comprising a vent in said ampule body adjacent to said connecting rod.

9. A self-contained disposable ampule, comprising:

a thin-walled, elongate plastic body with an opening at a first end and an internal electrically actuated propellant powder at a second end; and a piston slidably and sealingly mounted within said body entirely between said first end opening and said internal propellant powder and in contact with the sidewall of the body, said piston and said body together defining a medicine chamber and a combustion chamber within said ampule.

10. The ampule of claim 9, wherein said medicine chamber and combustion chamber have expandable sidewalls of insufficient strength to independently withstand normal peak operating pressures developed during an injection.

11. The ampule of claim 10, wherein said propellant powder is a biodegradable powder.

12. The ampule of claim 11, wherein said propellant powder is contained within a chamber mounted off-center in said elongate body with respect to the longitudinal axis thereof.

13. The ampule of claim 12, further comprising a preset dosage of medicine contained within said medicine chamber.

14. The ampule of claim 9, wherein said propellant powder is a biodegradable powder.

15. The ampule of claim 9, wherein said propellant powder is contained within a chamber mounted off-center in said elongate body with respect to the longitudinal axis thereof.

16. The ampule of claim 9, further comprising a preset dosage of medicine contained within said medicine chamber.

* * * * *